United States Patent [19]

Fisher et al.

[11] Patent Number: 5,507,904
[45] Date of Patent: Apr. 16, 1996

[54] METHOD OF MAKING A MEDICAL CONTAINER PORT TANGENTIAL TO THE CONTAINER

[75] Inventors: David P. Fisher; Allen R. Wons, both of Antioch, Ill.

[73] Assignee: Baxter International Inc., Deerfield, Ill.

[21] Appl. No.: 313,560

[22] Filed: Sep. 27, 1994

Related U.S. Application Data

[63] Continuation of Ser. No. 121,344, Sep. 14, 1993.

[51] Int. Cl.⁶ .................................................. B32B 31/00
[52] U.S. Cl. .................. 156/252; 156/274.4; 156/272.2; 156/308.2; 156/380.3; 53/479; 53/133.2; 53/DIG. 2; 206/828; 604/408
[58] Field of Search ............................. 156/272.2, 274.4, 156/250, 252, 293, 308.2, 380.3; 53/479, 133.1, 133.2, DIG. 2; 152/510, 511, 429, DIG. 11, DIG. 13; 40/586; 206/828; 604/408–415

[56] References Cited

U.S. PATENT DOCUMENTS

| | | |
|---|---|---|
| 2,816,596 | 12/1957 | Welch, Jr. . |
| 2,850,422 | 9/1958 | Welch, Jr. . |
| 2,949,712 | 8/1960 | Bieberdorf . |
| 3,030,955 | 4/1962 | Gossett . |
| 3,244,576 | 4/1966 | Swartz . |
| 3,403,064 | 9/1968 | Bellamy . |
| 3,576,650 | 4/1971 | Underwood . |
| 3,642,047 | 2/1972 | Waage . |
| 3,706,620 | 12/1972 | Dykstra . |
| 4,425,177 | 1/1984 | Shinno . |
| 4,484,904 | 11/1984 | Fowler . |
| 4,596,657 | 6/1986 | Wisdom . |
| 4,609,369 | 9/1986 | Ball . |
| 4,636,412 | 1/1987 | Field . |
| 4,650,452 | 3/1987 | Jensen . |
| 4,767,541 | 8/1988 | Wisdom . |
| 4,810,378 | 3/1989 | Carmen . |
| 4,855,063 | 8/1989 | Carmen . |
| 4,876,788 | 10/1989 | Steer . |
| 4,950,347 | 8/1990 | Futagawa . |
| 4,954,678 | 9/1990 | Harmony . |
| 4,997,577 | 3/1991 | Stewart . |
| 5,141,508 | 8/1992 | Bark et al. . |
| 5,190,657 | 3/1993 | Heagle . |
| 5,203,943 | 4/1993 | Nornberg et al. . |
| 5,205,895 | 4/1993 | Hohman, Jr. et al. . |
| 5,226,564 | 7/1993 | Steer et al. . |

FOREIGN PATENT DOCUMENTS

| | | |
|---|---|---|
| 0225828 | 6/1987 | European Pat. Off. . |
| 0365676 | 5/1990 | European Pat. Off. . |
| 0372074 | 6/1990 | European Pat. Off. . |
| 526678 | 2/1993 | European Pat. Off. . |
| 1334555 | 10/1973 | United Kingdom . |

*Primary Examiner*—James Engel
*Attorney, Agent, or Firm*—Daniel D. Ryan; Bradford R. L. Price; Joseph B. Barrett

[57] ABSTRACT

A port is formed in a thermoplastic container wall by slitting the wall, inserting a thermoplastic tube through the slit, placing a mandrel in the tube, placing opposed dies defining a bore over the sheet and tube, and dielectrically heating the thermoplastic to fuse the tube and sheet. Preferably the bore defined by the dies is of a diameter slightly less than that of the tube, and has an enlarged central area which forms a thickened section of material over the slit.

6 Claims, 3 Drawing Sheets

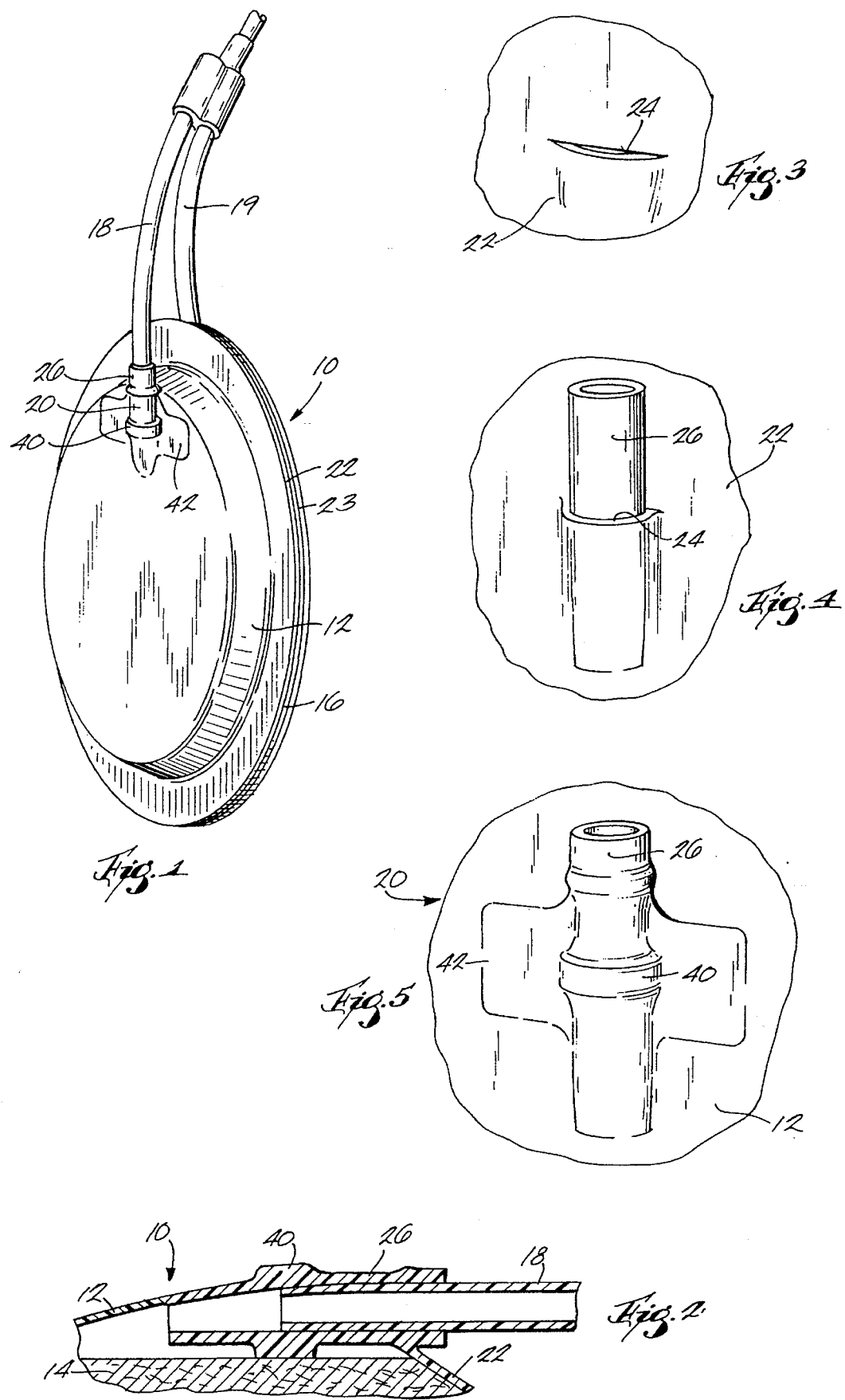

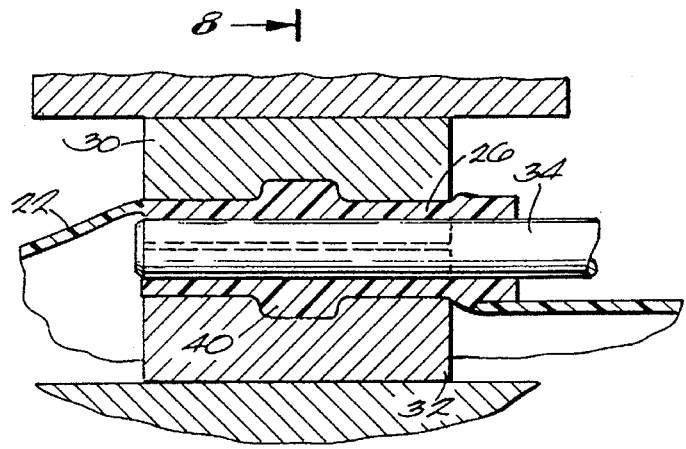
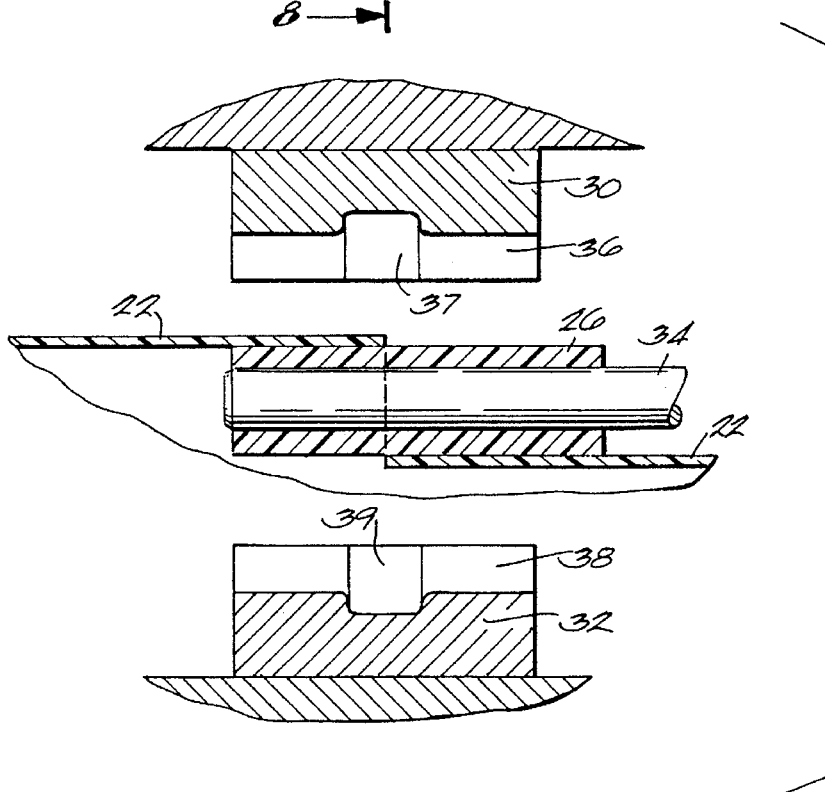
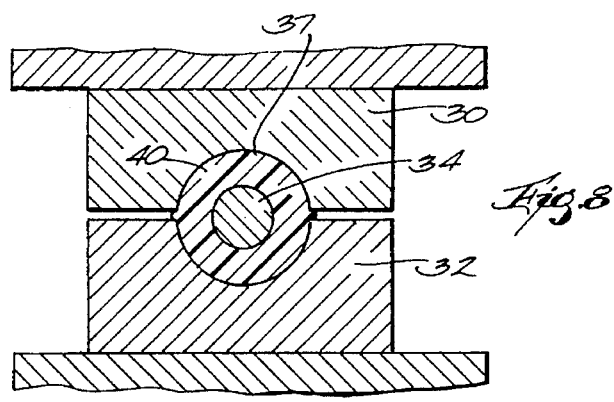

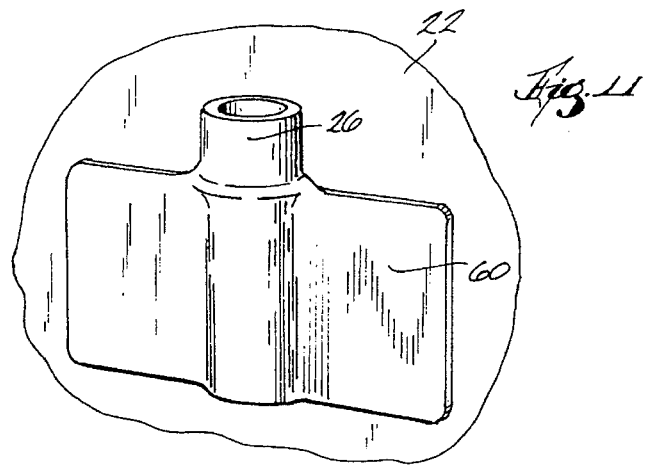
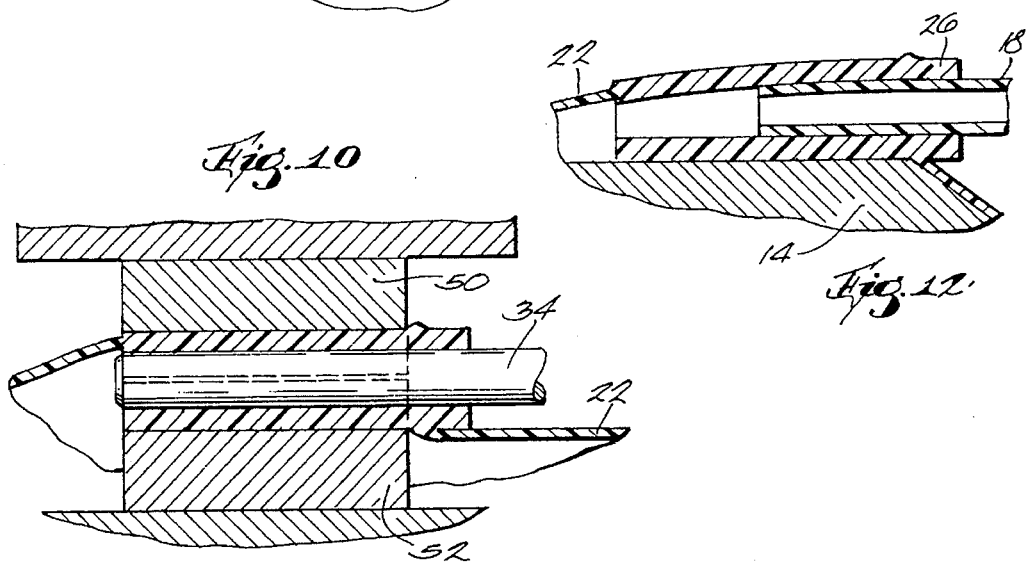
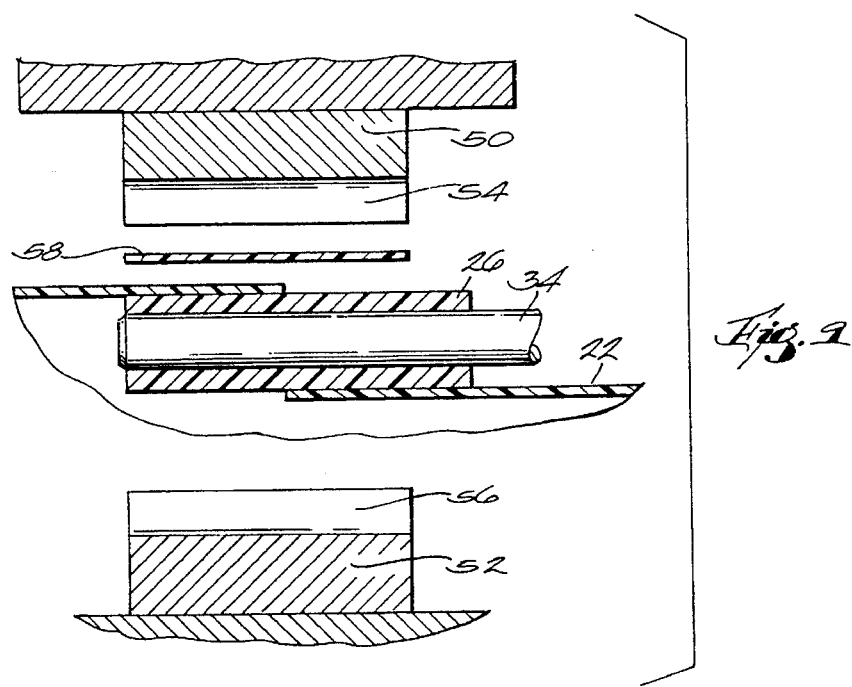

5,507,904

METHOD OF MAKING A MEDICAL CONTAINER PORT TANGENTIAL TO THE CONTAINER

This is a continuation of copending application(s) Ser. No. 08/121,344 filed on Sep. 14, 1993.

The present invention relates to an improved port for a housing such as a medical products container. More specifically, the invention relates to a port which is tangentially oriented with respect to a wall panel of a flexible container, for example, a blood bag or a fluid filter housing and a method of forming the same.

BACKGROUND OF THE INVENTION

It is common in the formation of medical products containers, such as blood bags or blood filtration housings containing filters, to form an opening in the peripheral seal of the container. Such openings may be in the form of a preformed tube that is heat sealed into the periphery of such a container. An example of such an opening is shown in European Patent Publication No. 526678 published Feb. 10, 1993, in which shows ports molded into the seal of such a container formed of two peripherally sealed halves. Alternatively, ports have been molded into a wall panel and oriented at a 90° angle to the plane of the panel.

Examples of filtration systems to remove white blood cells by filtration, for example, within the context of conventional multiple blood bag closed system configurations are described in Wisdom U.S. Pat. Nos. 4,596,657 and 4,767,541, as well as in Carmen et al U.S. Pat. Nos. 4,810,378 and 4,855,063. In these arrangements, an in-line white blood cell filtration device is used. Other such systems are described in Stewart U.S. Pat. No. 4,997,577. In these filtration systems white blood cells are removed as the red blood cells are conveyed to a transfer container. An example of a material used as a filter is set forth in Heagle et al U.S. Pat. No. 5,190,657 granted Mar. 2, 1993.

A need has existed for an improved opening port for plastic container walls used for a wide variety of purposes including such white blood cell filters. A particular need has existed for a form of a fluid pressure resistant outlet that can be formed tangentially in a flexible wall of a container.

SUMMARY OF THE INVENTION

It is a principle object of the present invention to provide an improved opening through a wall of a container such as a flexible bag for fluid materials, for example, medical products including blood or other body fluids or medicines.

In accordance with an important specific application of the invention, an opening is provided into a blood filtration housing such as those used to remove leukocytes from blood. An important aspect is to provide an opening into such a housing that maximizes the surface area of the filter material available for the filtration function. In accordance with the invention, an opening is provided in a side panel of the housing thus permitting the filter material to extend to the periphery of the housing. In accordance with a related aspect, the need to bring a port through a peripheral seal in a filter housing is eliminated. The latter aspect is particularly important when it is desired to seal the periphery of the filter material itself into the periphery of the filter housing.

In accordance with a still further aspect of the invention, a method for providing opening ports sealed into a container wall is provided. It is a yet further aspect of the invention to provide an opening through a panel of a container, which panel can subsequently be assembled by peripheral sealing to another panel to form an enclosed container structure.

In accordance with a yet further aspect of the invention, a port can be provided in a container panel which is aligned tangentially or approximately parallel to a surface of the panel.

In accordance with the preferred method of the present invention, a plastic tube is inserted in a slit formed in a plastic sheet formed of a material that can be softened to a flowable state by means of dielectric heated. The tube and sheet are then sealed together using contact dies that shape the plastic material softened by dielectric heating.

In accordance with the invention, a pair of opposed dies provided with a bore formed in their adjoining surfaces are positioned over a plastic tube placed in a slit in a sheet. The dies, which are formed of an electrically conductive material are positioned so that the bore that engages the opposite sides of the tubing. In accordance with a preferred embodiment of the invention the bore is provided with an undercut or enlarged central channel or groove that is positioned directly over the slit. The bore is preferably somewhat undersized in relation to the outer diameter of the tube inserted in the slit. When RF energy is transmitted to the plastic material through the conductive dies and a mandel inserted in the tube, the plastic material is caused to soften or melt and to flow to conform to the shape of the opposed dies. The central groove provides a channel into which flow of the softened plastic material of the tube occurs. Thus a reinforcing ridge or thickening located over the slit is provided. In accordance with the preferred method the mandrel inserted into the tube during heating maintains the shape and integrity of the opening port.

In accordance with an alternative embodiment of the invention, opposed dies having a central bore approximately the diameter of the tube can be used. In the alternative embodiment, a patch of plastic material is placed over the area of the slit in order to provide reinforcement or sufficient plastic material to ensure a sound leak-free seal capable of withstanding considerable fluid pressures.

Further advantages and aspects of the invention will be apparent from the following detailed description and accompanying drawings.

BRIEF DESCRIPTION OF THE DRAWINGS

FIG. 1 is a perspective view of a blood filter incorporating the invention;

FIG. 2 is a fragmentary cross-sectional view taken centrally through the port in the wall of the filter assembly of FIG. 1;

FIG. 3 is a fragmentary view of sheet of material showing an initial step in the manufacture of an opening in accordance with the invention;

FIG. 4 is a fragmentary view showing a further step in the manufacturing of an opening through the sheet material shown in FIG. 3;

FIG. 5 is a fragmentary view showing the finished port opening in accordance with a preferred embodiment of the invention;

FIG. 6 is a central sectional view showing the components in the manufacture of an opening in accordance with the invention prior to heating thereof;

FIG. 7 is a sectional view of the components shown in FIG. 6 during the heating step;

FIG. 8 is a sectional view taken along line 8–8 of FIG. 7;

FIG. 9 is a sectional view showing the assembly of apparatus and materials used in the formation of an opening in accordance with a further embodiment of the invention;

FIG. 10 is a sectional view of the materials shown in FIG. 9 during the molding operation;

FIG. 11 is a perspective view taken from the top of the opening formed in accordance with

FIG. 10; and

FIG. 12 is a central sectional view showing the port of FIG. 11 with tubing attached thereto.

DETAILED DESCRIPTION OF THE DRAWINGS

Referring more particularly to the drawings there is seen in FIG. 1 a blood filter assembly 10 used for purposes of illustration of an application of the invention and not by way of limitation. Numerous other applications of the invention will be apparent to those skilled in the art. Filter assembly 10 includes an outer housing 12 and an enclosed filter material 14 for filtration, for example, of white blood cells from whole blood. The outer perimeter 16 of housing 12 is heat sealed to form an enclosure. If desired, the filter material 14 can itself be partially heat sealed into the sealed perimeter of the enclosure. Flexible plastic or rubber tubing 18 and 19 can be attached to a port 20 by conventional means. Housing 12 is preferably formed from two sheets of thermoplastic material 22 and 23 that are fused peripherally together by heat and pressure.

The method of forming a port of this invention are shown in detail in FIGS. 3–8. As seen in FIG. 3, sheet of thermoplastic material susceptible to softening by application of RF energy is provided. Sheet 22 can be of any desired shape such as circular, square or oblong dependent on the shape of the container being formed. A slit 24 is formed in sheet 22 at a location spaced from the periphery of sheet 22. Slit 24 is made of a length to just accept the outer diameter of a tube 26 of thermoplastic material.

As seen in FIGS. 6–8, a pair of opposed dies 30 and 32 are positioned on opposite sides of slit 24 and tubing 26. A mandrel 34 having an outer diameter equal to the inner diameter of tube 26 is inserted within tube 26 as seen in FIGS. 6 and 7. Dies 30 and 32 are provided with aligned concave recesses 36 and 38 that together form a circular bore. Central grooves 37 and 39 are formed in recesses 36 and 38, respectively. The sheet 22, dies 30 and 32, tubing 26 and mandrel 34 are all brought together into the position shown in FIG. 7. Preferably a stop is provided to accurately space dies 30 and 32 apart from each other. RF energy is, then, supplied through dies 30 and 32 and mandrel 34 in order to soften the thermoplastic material of tube 26 and sheet 22. Dies 30 and 32, which remain relatively cool, act as a mold for the softened material. Material from tube 26 flows as indicated into grooves 37 and 39 to form an enlargement of material or ridge 40 that serves to reinforce the junction between tube 26 and slit 24 in sheet 22. A depression 42 of slightly decreased thickness is formed in the sheet 22 surrounding the completed port 20. The resultant port opening 20 is, thus, reinforced at its potentially weakest point and is capable of withstanding substantial pressure. After a brief period of cooling, the thermoplastic material hardens sufficiently and dies 30 and 32 and mandrel 34 can be withdrawn.

In the alternate embodiment shown in FIGS. 9–12, dies 50 and 52 having concave recesses 54 and 56, respectively, are utilized. In this embodiment, a patch 58 of thermoplastic material is used to ensure adequate amounts of thermoplastic material to provide a pressure-tight seal. The resultant seal seen in FIG. 12 does not have a thickened central portion. Portion 60 surrounding the port represents a depression wherein sheet 22 is of slightly reduced thickness defined by the opposed dies 50 and 52.

After the port is thus formed in sheet 22 by one of the foregoing procedures, the sheet can subsequently be peripherally bonded to form the finished container. Tubing 18 and 19 can be applied by any known method, for example, adhesive bonding.

While the formation of a blood filter is shown for purposes of illustration, the invention is equally applicable to formation of other containers for medical products, for example, blood bags or IV solution containers.

It is preferred that the sheet 22 be formed of polyvinylchloride which is selected because of its receptiveness to dielectric heat sealing. Such materials can be modified by addition of various plasticizers and are readily sterilized using conventional sterilization methods. An examples of another material that can be used is ethylene vinyl acetate.

In a preferred example of the use of the invention, sheet 22 is formed of polyvinylchloride having a thickness of 0.015 inch. A port tube having a wall thickness of 0.02 inch, an outside of 0.228 inch and a length of 0.75 inch is used. Mandrel 34 is preferably 0.003 inch smaller than the inner diameter of the tube and the mandrel tip extends approximately 0.30 inch beyond the end of the tube 26.

RF energy is applied for the dielectric heating step through a switching mechanism which first feeds the energy to the mandrel 34 and then to the opposing dies 30 and 32. Preferably, a mechanical stop is used to ensure that the two dies are separated by 0.012 inch. Since the dies are not greatly heated by the dielectric heating, they can be withdrawn after a brief cooling period.

In accordance with the invention, a tubing is generally preferred that has a wall thickness of approximately 20–70% thicker than the film. This ensures that an adequate amount of thermoplastic material is available to form rib 40 in the finished port opening joint. It is also preferred that slit 24 be no longer than the diameter of the tubing thereby ensuring a tight initial fit between the sheet 22 and tubing 26. The film surrounding the opening port 20 is preferably at least 80% of the original thickness of the film. The wall of tubing 26 is thinned to approximately 60–70% of the original thickness.

It is, thus, seen that port opening in a container can be formed that is generally tangential or parallel to the wall of the container. In the case of a filter housing 10, the available surface area of the filter is maximized since the filter itself extends to the periphery without adversely affecting fluid flow in and out of the filter housing.

Other modifications of the invention within the ability of those skilled in the art can be made without departing from the true scope of the appended claims.

What is claimed is:

1. A method of forming a port in a thermoplastic sheet which forms a wall of a thermoplastic container comprising the steps of:

providing a sheet of thermoplastic material, forming a slit in said sheet at a position spaced from the periphery thereof, inserting a hollow tube of thermoplastic material through said slit so that one end of said tube is located on each side of said sheet, heat fusing said sheet around said tube so that said tube defines an opening through said sheet and said tube is oriented tangentially to the surface of said sheet, and subsequently forming said sheet into said container.

2. A method according to claim 1 wherein the periphery of said sheet is heat sealed to the periphery of another sheet 3. A method according to claim 1 wherein said fusing step is conducted by placing metallic dies on opposite sides of said tube, a mandrel in the bore of said tube, and applying energy thereto to dielectrically heat said tube and thermoplastic sheet to cause softening thereof.

4. A method according to claim 3 wherein said die comprises two halves defining a cylindrical bore adapted to engage the opposite sides of said tube and wherein a central transverse enlargement is provided in said bore and wherein said enlargement is positioned on opposite sides of said slit during said heat fusing step whereby a thickened section of fused material is formed over said slit.

5. A method according to claim 4 wherein said bore has a diameter slightly less than the outer diameter of said tube.

6. A method according to claim 1 wherein said thermoplastic material is dielectrically heated by application of radio frequency energy thereto.

* * * * *